United States Patent
Ohto et al.

(10) Patent No.: US 9,714,436 B2
(45) Date of Patent: Jul. 25, 2017

(54) RECOMBINANT MICROORGANISM AND METHOD FOR PRODUCING A SUBSTANCE USING THE SAME

(71) Applicants: TOYOTA JIDOSHA KABUSHIKI KAISHA, Toyota-shi, Aichi (JP); KYOTO UNIVERSITY, Kyoto-shi, Kyoto (JP)

(72) Inventors: Chikara Ohto, Toyota (JP); Masayoshi Muramatsu, Miyoshi (JP); Masakazu Ito, Toyota (JP); Jun Ogawa, Kyoto (JP); Shigenobu Kishino, Muko (JP)

(73) Assignees: TOYOTA JIDOSHA KABUSHIKI KAISHA, Toyota-shi, Aichi (JP); KYOTO UNIVERSITY, Kyoto-shi, Kyoto (JP)

( * ) Notice: Subject to any disclaimer, the term of this patent is extended or adjusted under 35 U.S.C. 154(b) by 0 days.

(21) Appl. No.: 14/717,019

(22) Filed: May 20, 2015

(65) Prior Publication Data
US 2015/0344913 A1    Dec. 3, 2015

(30) Foreign Application Priority Data

May 30, 2014   (JP) ................................ 2014-112575

(51) Int. Cl.
*C12P 5/02* (2006.01)
*C12P 7/04* (2006.01)

(52) U.S. Cl.
CPC ........ *C12P 5/02* (2013.01); *C12P 7/04* (2013.01); *C12Y 102/0105* (2013.01)

(58) Field of Classification Search
None
See application file for complete search history.

(56) References Cited

U.S. PATENT DOCUMENTS

| | | |
|---|---|---|
| 6,610,836 B1 | 8/2003 | Breton et al. |
| 8,415,136 B1 | 4/2013 | Gardner et al. |
| 2013/0130344 A1 | 5/2013 | Lee et al. |

FOREIGN PATENT DOCUMENTS

| | | | |
|---|---|---|---|
| JP | 2002-223788 A | | 8/2002 |
| JP | 2010-528627 A | | 8/2010 |
| JP | 2011-512848 A | | 4/2011 |
| JP | 2011-520455 A | | 7/2011 |
| JP | 2012-506715 A | | 3/2012 |
| JP | 2012-511928 A | | 5/2012 |
| JP | 2013-528057 A | | 7/2013 |
| WO | 2008/151149 A2 | | 12/2008 |
| WO | WO 2009/013159 | * | 1/2009 |
| WO | 2009/111672 A1 | | 9/2009 |
| WO | 2009/140696 A2 | | 11/2009 |
| WO | 2010/062480 A2 | | 6/2010 |
| WO | 2010/071697 A1 | | 6/2010 |

OTHER PUBLICATIONS

Schirmer et al., "Microbial Biosynthesis of Alkanes", Science, Jul. 2010, 329: 559-562. doi: 10.1126/science.1187936.*

* cited by examiner

*Primary Examiner* — Suzanne M Noakes
(74) *Attorney, Agent, or Firm* — Sughrue Mion, PLLC

(57) ABSTRACT

This invention provides a recombinant microorganism into which an acyl-CoA reductase exerting excellent activity in a reduction reaction involving the use of acyl-CoA as a substrate has been introduced. Such recombinant microorganism comprises a nucleic acid encoding a protein (a) or (b) below introduced into a host microorganism: (a) a protein comprising the amino acid sequence of SEQ ID NO: 2; or (b) a protein comprising an amino acid sequence having 70% or higher identity to the amino acid sequence of SEQ ID NO: 2 and having activity for synthesizing an aldehyde compound from acyl-CoA.

9 Claims, 2 Drawing Sheets

SEQUENCE LISTING

<160> NUMBER OF SEQ ID NOS: 17

<210> SEQ ID NO 1
<211> LENGTH: 1404
<212> TYPE: DNA
<213> ORGANISM: Klebsiella Pneumoniae Subsp. Pneumoniae NBRC3321
<220> FEATURE:
<221> NAME/KEY: CDS
<222> LOCATION: (1)..(1404)

<400> SEQUENCE: 1

| | | | | | | | | | | | | | | | | |
|---|---|---|---|---|---|---|---|---|---|---|---|---|---|---|---|---|
| atg | aat | caa | cag | gac | atc | gaa | caa | gtc | gtg | aag | gca | gtt | ctg | ctg | aaa | 48 |
| Met | Asn | Gln | Gln | Asp | Ile | Glu | Gln | Val | Val | Lys | Ala | Val | Leu | Leu | Lys | |
| 1 | | | | 5 | | | | | 10 | | | | | 15 | | |
| atg | aag | gac | tcg | tcg | caa | ccg | gcg | ggc | acc | gtg | cat | gac | atg | ggc | gtg | 96 |
| Met | Lys | Asp | Ser | Ser | Gln | Pro | Ala | Gly | Thr | Val | His | Asp | Met | Gly | Val | |
| | | | 20 | | | | | 25 | | | | | 30 | | | |
| ttc | gct | tcc | ctg | gat | gac | gct | gtg | gcg | gca | gcc | acc | gtt | gct | cag | caa | 144 |
| Phe | Ala | Ser | Leu | Asp | Asp | Ala | Val | Ala | Ala | Ala | Thr | Val | Ala | Gln | Gln | |
| | | | | 35 | | | | | 40 | | | | | 45 | | |
| ggt | ctg | aaa | cgc | gtt | gca | atg | cgt | cag | caa | gtc | atc | cag | gca | att | cgc | 192 |
| Gly | Leu | Lys | Arg | Val | Ala | Met | Arg | Gln | Gln | Val | Ile | Gln | Ala | Ile | Arg | |
| | 50 | | | | | 55 | | | | | 60 | | | | | |
| gaa | gcc | ggc | gag | aag | tac | gcg | cgt | gaa | ctg | gct | gag | ctg | gcg | gtg | acc | 240 |
| Glu | Ala | Gly | Glu | Lys | Tyr | Ala | Arg | Glu | Leu | Ala | Glu | Leu | Ala | Val | Thr | |
| 65 | | | | | 70 | | | | | 75 | | | | | 80 | |
| gaa | acc | ggc | atg | ggt | cgc | gtt | gag | gat | aaa | ttt | gca | aag | aac | gtc | gct | 288 |
| Glu | Thr | Gly | Met | Gly | Arg | Val | Glu | Asp | Lys | Phe | Ala | Lys | Asn | Val | Ala | |
| | | | | 85 | | | | | 90 | | | | | 95 | | |
| cag | gca | cgt | ggc | acc | cca | ggt | gtg | gaa | tgc | ctg | acc | cct | caa | gtt | ctg | 336 |
| Gln | Ala | Arg | Gly | Thr | Pro | Gly | Val | Glu | Cys | Leu | Thr | Pro | Gln | Val | Leu | |
| | | | 100 | | | | | 105 | | | | | 110 | | | |
| acc | ggc | gat | aac | ggt | ctg | acc | ctg | atc | gaa | aat | gca | ccg | tgg | ggt | gtg | 384 |
| Thr | Gly | Asp | Asn | Gly | Leu | Thr | Leu | Ile | Glu | Asn | Ala | Pro | Trp | Gly | Val | |
| | | | | 115 | | | | | 120 | | | | | 125 | | |
| gtt | gcc | tcc | gtc | acc | ccg | agc | acc | aac | cca | gct | gcg | acc | gtg | att | aac | 432 |
| Val | Ala | Ser | Val | Thr | Pro | Ser | Thr | Asn | Pro | Ala | Ala | Thr | Val | Ile | Asn | |
| | 130 | | | | | 135 | | | | | 140 | | | | | |
| aat | gcc | atc | tct | ctg | att | gca | gcc | ggc | aat | tca | gtc | gtg | ttc | gcg | cct | 480 |
| Asn | Ala | Ile | Ser | Leu | Ile | Ala | Ala | Gly | Asn | Ser | Val | Val | Phe | Ala | Pro | |
| 145 | | | | | 150 | | | | | 155 | | | | | 160 | |
| cac | ccg | gct | gcg | aaa | aag | gtg | tct | cag | cgc | gct | atc | acc | ctg | ctg | aac | 528 |
| His | Pro | Ala | Ala | Lys | Lys | Val | Ser | Gln | Arg | Ala | Ile | Thr | Leu | Leu | Asn | |
| | | | | 165 | | | | | 170 | | | | | 175 | | |
| caa | gct | gtt | gtc | gca | gcc | ggc | ggt | cct | gca | aac | ctg | ctg | gtc | acc | gtg | 576 |
| Gln | Ala | Val | Val | Ala | Ala | Gly | Gly | Pro | Ala | Asn | Leu | Leu | Val | Thr | Val | |
| | | | 180 | | | | | 185 | | | | | 190 | | | |
| gcc | aat | cca | gat | atc | gac | acc | gct | cag | cgt | ctg | ttt | aaa | tat | ccg | ggc | 624 |
| Ala | Asn | Pro | Asp | Ile | Asp | Thr | Ala | Gln | Arg | Leu | Phe | Lys | Tyr | Pro | Gly | |
| | | | | 195 | | | | | 200 | | | | | 205 | | |
| att | ggt | ctg | ctg | gtt | gtg | acc | ggc | ggt | gaa | gct | gtc | gtg | gag | gct | gct | 672 |
| Ile | Gly | Leu | Leu | Val | Val | Thr | Gly | Gly | Glu | Ala | Val | Val | Glu | Ala | Ala | |
| | 210 | | | | | 215 | | | | | 220 | | | | | |
| cgc | aaa | cat | acc | aac | aag | cgt | ctg | att | gca | gcc | ggc | gcg | ggt | aat | ccg | 720 |
| Arg | Lys | His | Thr | Asn | Lys | Arg | Leu | Ile | Ala | Ala | Gly | Ala | Gly | Asn | Pro | |
| 225 | | | | | 230 | | | | | 235 | | | | | 240 | |
| cca | gtt | gtc | gtg | gat | gaa | acc | gca | gac | ctg | cca | cgc | gct | gct | cag | gca | 768 |
| Pro | Val | Val | Val | Asp | Glu | Thr | Ala | Asp | Leu | Pro | Arg | Ala | Ala | Gln | Ala | |
| | | | | 245 | | | | | 250 | | | | | 255 | | |
| atc | gtg | aaa | ggt | gcc | agc | ttc | gat | aac | aat | atc | att | tgt | gcc | gac | gaa | 816 |
| Ile | Val | Lys | Gly | Ala | Ser | Phe | Asp | Asn | Asn | Ile | Ile | Cys | Ala | Asp | Glu | |

-continued

|  |  |  | 260 |  |  | 265 |  |  |  | 270 |  |  |  |  |
|---|---|---|---|---|---|---|---|---|---|---|---|---|---|---|
| aag | gtc | ctg | att | gtt | gtc | gat | tct | gtg | gct | gac | gaa | ctg | atg cgc ctg | 864 |
| Lys | Val | Leu | Ile | Val | Val | Asp | Ser | Val | Ala | Asp | Glu | Leu | Met Arg Leu |  |
|  |  | 275 |  |  |  | 280 |  |  |  | 285 |  |  |  |  |

| atg | gag | ggc | cag | caa | gcc | gtt | aaa | ctg | acc | gca | gcc | cag | gct gaa cag | 912 |
| Met | Glu | Gly | Gln | Gln | Ala | Val | Lys | Leu | Thr | Ala | Ala | Gln | Ala Glu Gln |  |
|  | 290 |  |  |  | 295 |  |  |  | 300 |  |  |  |  |  |

| ctg | caa | cca | ctg | ctg | ctg | aaa | aac | atc | gat | gag | cgt | ggc | aag ggt acc | 960 |
| Leu | Gln | Pro | Leu | Leu | Leu | Lys | Asn | Ile | Asp | Glu | Arg | Gly | Lys Gly Thr |  |
| 305 |  |  |  | 310 |  |  |  | 315 |  |  |  |  | 320 |  |

| gtc | tca | cgc | gat | tgg | gtg | ggc | cgt | gac | gca | ggc | aag | atc | gct gcg gca | 1008 |
| Val | Ser | Arg | Asp | Trp | Val | Gly | Arg | Asp | Ala | Gly | Lys | Ile | Ala Ala Ala |  |
|  |  |  | 325 |  |  |  | 330 |  |  |  | 335 |  |  |  |

| att | ggt | ctg | cag | gtg | cct | gct | caa | acc | cgt | ctg | ctg | ttc | gtt gaa acc | 1056 |
| Ile | Gly | Leu | Gln | Val | Pro | Ala | Gln | Thr | Arg | Leu | Leu | Phe | Val Glu Thr |  |
|  |  | 340 |  |  |  | 345 |  |  |  | 350 |  |  |  |  |

| cct | gct | agc | cac | ccg | ttt | gcg | gtt | acc | gag | ctg | atg | atg | cca gtc ctg | 1104 |
| Pro | Ala | Ser | His | Pro | Phe | Ala | Val | Thr | Glu | Leu | Met | Met | Pro Val Leu |  |
|  | 355 |  |  |  | 360 |  |  |  | 365 |  |  |  |  |  |

| cct | gtg | gtt | cgt | gtt | gcc | aac | gtc | gaa | gag | gcc | atc | gct | ctg gcg gtg | 1152 |
| Pro | Val | Val | Arg | Val | Ala | Asn | Val | Glu | Glu | Ala | Ile | Ala | Leu Ala Val |  |
| 370 |  |  |  | 375 |  |  |  | 380 |  |  |  |  |  |  |

| cag | ctg | gaa | ggc | ggt | tgc | cac | cat | acc | gcc | gct | atg | cat | tcg cgc aac | 1200 |
| Gln | Leu | Glu | Gly | Gly | Cys | His | His | Thr | Ala | Ala | Met | His | Ser Arg Asn |  |
| 385 |  |  |  | 390 |  |  |  | 395 |  |  |  |  | 400 |  |

| atc | gat | aac | atg | aac | caa | atg | gca | aac | gcc | atc | gac | acc | agc att ttt | 1248 |
| Ile | Asp | Asn | Met | Asn | Gln | Met | Ala | Asn | Ala | Ile | Asp | Thr | Ser Ile Phe |  |
|  |  |  | 405 |  |  |  | 410 |  |  |  | 415 |  |  |  |

| gtt | aaa | aat | ggc | cct | tgt | atc | gca | ggc | ctg | ggt | ctg | ggc | ggt gaa ggt | 1296 |
| Val | Lys | Asn | Gly | Pro | Cys | Ile | Ala | Gly | Leu | Gly | Leu | Gly | Gly Glu Gly |  |
|  |  | 420 |  |  |  | 425 |  |  |  | 430 |  |  |  |  |

| tgg | acc | acc | atg | acc | att | acc | acc | ccg | acc | ggc | gag | ggt | gtc acc tct | 1344 |
| Trp | Thr | Thr | Met | Thr | Ile | Thr | Thr | Pro | Thr | Gly | Glu | Gly | Val Thr Ser |  |
|  | 435 |  |  |  | 440 |  |  |  | 445 |  |  |  |  |  |

| gca | cgt | acc | ttt | gtt | cgt | ctg | cgt | cgc | tgt | gtt | ctg | gtt | gat gcc ttt | 1392 |
| Ala | Arg | Thr | Phe | Val | Arg | Leu | Arg | Arg | Cys | Val | Leu | Val | Asp Ala Phe |  |
| 450 |  |  |  | 455 |  |  |  | 460 |  |  |  |  |  |  |

| cgt | atc | gtc | taa |  |  |  |  |  |  |  |  |  |  | 1404 |
| Arg | Ile | Val |  |  |  |  |  |  |  |  |  |  |  |  |
| 465 |  |  |  |  |  |  |  |  |  |  |  |  |  |  |

<210> SEQ ID NO 2
<211> LENGTH: 467
<212> TYPE: PRT
<213> ORGANISM: Klebsiella Pneumoniae Subsp. Pneumoniae NBRC3321

<400> SEQUENCE: 2

Met Asn Gln Gln Asp Ile Glu Gln Val Val Lys Ala Val Leu Leu Lys
1               5                   10                  15

Met Lys Asp Ser Ser Gln Pro Ala Gly Thr Val His Asp Met Gly Val
            20                  25                  30

Phe Ala Ser Leu Asp Asp Ala Val Ala Ala Thr Val Ala Gln Gln
        35                  40                  45

Gly Leu Lys Arg Val Ala Met Arg Gln Gln Val Ile Gln Ala Ile Arg
    50                  55                  60

Glu Ala Gly Glu Lys Tyr Ala Arg Glu Leu Ala Glu Leu Ala Val Thr
65                  70                  75                  80

Glu Thr Gly Met Gly Arg Val Glu Asp Lys Phe Ala Lys Asn Val Ala
                85                  90                  95

-continued

```
Gln Ala Arg Gly Thr Pro Val Glu Cys Leu Thr Pro Gln Val Leu
                100                 105                 110
Thr Gly Asp Asn Gly Leu Thr Leu Ile Glu Asn Ala Pro Trp Gly Val
            115                 120                 125
Val Ala Ser Val Thr Pro Ser Thr Asn Pro Ala Ala Thr Val Ile Asn
130                 135                 140
Asn Ala Ile Ser Leu Ile Ala Ala Gly Asn Ser Val Val Phe Ala Pro
145                 150                 155                 160
His Pro Ala Ala Lys Lys Val Ser Gln Arg Ala Ile Thr Leu Leu Asn
                165                 170                 175
Gln Ala Val Val Ala Ala Gly Pro Ala Asn Leu Leu Val Thr Val
            180                 185                 190
Ala Asn Pro Asp Ile Asp Thr Ala Gln Arg Leu Phe Lys Tyr Pro Gly
                195                 200                 205
Ile Gly Leu Leu Val Val Thr Gly Gly Glu Ala Val Val Glu Ala Ala
210                 215                 220
Arg Lys His Thr Asn Lys Arg Leu Ile Ala Ala Gly Ala Gly Asn Pro
225                 230                 235                 240
Pro Val Val Val Asp Glu Thr Ala Asp Leu Pro Arg Ala Ala Gln Ala
                245                 250                 255
Ile Val Lys Gly Ala Ser Phe Asp Asn Asn Ile Ile Cys Ala Asp Glu
            260                 265                 270
Lys Val Leu Ile Val Val Asp Ser Val Ala Asp Glu Leu Met Arg Leu
        275                 280                 285
Met Glu Gly Gln Gln Ala Val Lys Leu Thr Ala Ala Gln Ala Glu Gln
    290                 295                 300
Leu Gln Pro Leu Leu Leu Lys Asn Ile Asp Glu Arg Gly Lys Gly Thr
305                 310                 315                 320
Val Ser Arg Asp Trp Val Gly Arg Asp Ala Gly Lys Ile Ala Ala Ala
                325                 330                 335
Ile Gly Leu Gln Val Pro Ala Gln Thr Arg Leu Leu Phe Val Glu Thr
            340                 345                 350
Pro Ala Ser His Pro Phe Ala Val Thr Glu Leu Met Met Pro Val Leu
        355                 360                 365
Pro Val Val Arg Val Ala Asn Val Glu Glu Ala Ile Ala Leu Ala Val
    370                 375                 380
Gln Leu Glu Gly Gly Cys His His Thr Ala Ala Met His Ser Arg Asn
385                 390                 395                 400
Ile Asp Asn Met Asn Gln Met Ala Asn Ala Ile Asp Thr Ser Ile Phe
                405                 410                 415
Val Lys Asn Gly Pro Cys Ile Ala Gly Leu Gly Leu Gly Gly Glu Gly
            420                 425                 430
Trp Thr Thr Met Thr Ile Thr Thr Pro Thr Gly Glu Gly Val Thr Ser
        435                 440                 445
Ala Arg Thr Phe Val Arg Leu Arg Arg Cys Val Leu Val Asp Ala Phe
    450                 455                 460
Arg Ile Val
465

<210> SEQ ID NO 3
<211> LENGTH: 467
<212> TYPE: PRT
<213> ORGANISM: Klebsiella pneumoniae CG43
```

<400> SEQUENCE: 3

Met Asn Gln Gln Asp Ile Glu Gln Val Lys Ala Val Leu Leu Lys
1               5                   10                  15

Met Lys Asp Ser Ser Gln Pro Ala Gly Thr Val His Asp Met Gly Val
            20                  25                  30

Phe Ala Ser Leu Asp Asp Ala Val Ala Ala Thr Val Ala Gln Gln
            35                  40                  45

Gly Leu Lys Arg Val Ala Met Arg Gln Val Ile Gln Ala Ile Arg
    50                  55                  60

Glu Ala Gly Glu Lys Tyr Ala Arg Glu Leu Ala Glu Leu Ala Val Thr
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Thr Pro Gln Val Leu
            100                 105                 110

Thr Gly Asp Asn Gly Leu Thr Leu Ile Glu Asn Ala Pro Trp Gly Val
            115                 120                 125

Val Ala Ser Val Thr Pro Ser Thr Asn Pro Ala Ala Thr Val Ile Asn
            130                 135                 140

Asn Ala Ile Ser Leu Ile Ala Ala Gly Asn Ser Val Val Phe Ala Pro
145                 150                 155                 160

His Pro Ala Ala Lys Lys Val Ser Gln Arg Ala Ile Thr Leu Leu Asn
                165                 170                 175

Gln Ala Val Val Ala Ala Gly Gly Pro Ala Asn Leu Leu Val Thr Val
            180                 185                 190

Ala Asn Pro Asp Ile Asp Thr Ala Gln Arg Leu Phe Lys Tyr Pro Gly
            195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Pro Arg Ala Ala Gln Ala
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
            275                 280                 285

Met Glu Gly Gln Gln Ala Val Lys Leu Thr Ala Ala Gln Ala Glu Gln
290                 295                 300

Leu Gln Pro Leu Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Gln Val Pro Ala Gln Thr Arg Leu Leu Phe Val Glu Thr
            340                 345                 350

Pro Ala Ser His Pro Phe Ala Val Thr Glu Leu Met Met Pro Val Leu
            355                 360                 365

Pro Val Val Arg Val Ala Asn Val Glu Glu Ala Ile Ala Leu Ala Val
            370                 375                 380

Gln Leu Glu Gly Gly Cys His His Thr Ala Ala Met His Ser Arg Asn
385                 390                 395                 400

Ile Asp Asn Met Asn Gln Met Ala Asn Ala Ile Asp Thr Ser Ile Phe
            405                 410                 415

```
Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
            435                 440                 445

Ala Arg Thr Phe Val Arg Leu Arg Arg Cys Val Leu Val Asp Ala Phe
450                 455                 460

Arg Ile Val
465

<210> SEQ ID NO 4
<211> LENGTH: 467
<212> TYPE: PRT
<213> ORGANISM: Klebsiella pneumoniae KCTC 2242

<400> SEQUENCE: 4

Met Asn Gln Gln Asp Ile Glu Gln Val Val Lys Ala Val Leu Leu Lys
1               5                   10                  15

Met Lys Asp Ser Ser Gln Pro Ala Gly Thr Val His Asp Met Gly Val
            20                  25                  30

Phe Ala Ser Leu Asp Asp Ala Val Ala Ala Thr Val Ala Gln Gln
            35                  40                  45

Gly Leu Lys Arg Val Ala Met Arg Gln Gln Val Ile Gln Ala Ile Arg
50                  55                  60

Glu Ala Gly Glu Lys Tyr Ala Arg Glu Leu Ala Glu Leu Ala Val Thr
65                  70                  75                  80

Glu Thr Gly Met Gly Arg Val Glu Asp Lys Phe Ala Lys Asn Val Ala
            85                  90                  95

Gln Ala Arg Gly Thr Pro Gly Val Glu Cys Leu Thr Pro Gln Val Leu
            100                 105                 110

Thr Gly Asp Asn Gly Leu Thr Leu Ile Glu Asn Ala Pro Trp Gly Val
            115                 120                 125

Val Ala Ser Val Thr Pro Ser Thr Asn Pro Ala Ala Thr Val Ile Asn
            130                 135                 140

Asn Ala Ile Ser Leu Ile Ala Ala Gly Asn Ser Val Val Phe Ala Pro
145                 150                 155                 160

His Pro Ala Ala Lys Lys Val Ser Gln Arg Ala Ile Thr Leu Leu Asn
            165                 170                 175

Gln Ala Val Val Ala Ala Gly Gly Pro Ala Asn Leu Leu Val Thr Val
            180                 185                 190

Ala Asn Pro Asp Ile Asp Thr Ala Gln Arg Leu Phe Lys Tyr Pro Gly
            195                 200                 205

Ile Gly Leu Leu Val Val Thr Gly Gly Glu Ala Val Val Glu Ala Ala
            210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Pro Arg Ala Ala Gln Ala
            245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
            275                 280                 285

Met Glu Gly Gln Gln Ala Val Lys Leu Thr Ala Ala Gln Ala Glu Gln
            290                 295                 300

Leu Gln Pro Leu Leu Leu Lys Asn Ile Asp Glu Arg Gly Lys Gly Thr
```

```
305                 310                 315                 320
Val Ser Arg Asp Trp Val Gly Arg Asp Ala Gly Lys Ile Ala Ala Ala
                325                 330                 335

Ile Gly Leu Gln Val Pro Ala Gln Thr Arg Leu Leu Phe Val Glu Thr
            340                 345                 350

Pro Ala Ser His Pro Phe Ala Val Thr Glu Leu Met Met Pro Val Leu
        355                 360                 365

Pro Val Val Arg Val Ala Asn Val Glu Glu Ala Ile Ala Leu Ala Val
    370                 375                 380

Gln Leu Glu Gly Gly Cys His His Thr Ala Ala Met His Ser Ser Asn
385                 390                 395                 400

Ile Asp Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465

<210> SEQ ID NO 5
<211> LENGTH: 467
<212> TYPE: PRT
<213> ORGANISM: Salmonella enterica subsp. enterica Serovar Heidelberg
      CFSAN002069

<400> SEQUENCE: 5

Met Asn Gln Gln Asp Ile Glu Gln Val Val Lys Ala Val Leu Leu Lys
1               5                   10                  15

Met Lys Asp Ser Ser Gln Pro Ala Ser Thr Val His Glu Met Gly Val
            20                  25                  30

Phe Ala Ser Leu Asp Asp Ala Val Ala Ala Lys Arg Ala Gln Gln
        35                  40                  45

Gly Leu Lys Ser Val Ala Met Arg Gln Leu Ala Ile His Ala Ile Arg
    50                  55                  60

Glu Ala Gly Glu Lys His Ala Arg Glu Leu Ala Glu Leu Ala Val Ser
65                  70                  75                  80

Glu Thr Gly Met Gly Arg Val Asp Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Val Phe Ala Pro
145                 150                 155                 160

His Pro Ala Ala Lys Lys Val Ser Gln Arg Ala Ile Thr Leu Leu Asn
                165                 170                 175

Gln Ala Val Val Ala Ala Gly Gly Pro Glu Asn Leu Leu Val Thr Val
            180                 185                 190

Ala Asn Pro Asp Ile Glu Thr Ala Gln Arg Leu Phe Lys Tyr Pro Gly
        195                 200                 205
```

```
Ile Gly Leu Leu Val Val Thr Gly Gly Glu Ala Val Val Asp Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Pro Arg Ala Ala Gln Ser
                245                 250                 255

Ile Val Lys Gly Ala Ser Phe Asp Asn Asn Ile Ile Cys Ala Asp Glu
                260                 265                 270

Lys Val Leu Ile Val Val Asp Ser Val Ala Asp Glu Leu Met Arg Leu
                275                 280                 285

Met Glu Gly Gln His Ala Val Lys Leu Thr Ala Ala Gln Ala Glu Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Asn Val Pro Asp Gln Thr Arg Leu Leu Phe Val Glu Thr
                340                 345                 350

Pro Ala Asn His Pro Phe Ala Val Thr Glu Leu Met Met Pro Val Leu
                355                 360                 365

Pro Val Val Arg Val Ala Asn Val Glu Glu Ala Ile Ala Leu Ala Val
                370                 375                 380

Gln Leu Glu Gly Gly Cys His His Thr Ala Ala Met His Ser Arg Asn
385                 390                 395                 400

Ile Asp Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
                420                 425                 430

Trp Thr Thr Met Thr Ile Thr Thr Pro Thr Gly Glu Gly Val Thr Ser
                435                 440                 445

Ala Arg Thr Phe Val Arg Leu Arg Arg Cys Val Leu Val Asp Ala Phe
    450                 455                 460

Arg Ile Val
465

<210> SEQ ID NO 6
<211> LENGTH: 467
<212> TYPE: PRT
<213> ORGANISM: Salmonella enterica subsp. enterica serovar Gallinarum
      287/91

<400> SEQUENCE: 6

Met Asn Gln Gln Asp Ile Glu Gln Val Val Lys Ala Val Leu Leu Lys
1               5                   10                  15

Met Lys Asp Ser Ser Gln Pro Ala Ser Thr Val His Glu Met Gly Val
                20                  25                  30

Phe Ala Ser Leu Asp Asp Ala Val Ala Ala Lys Arg Ala Gln Gln
                35                  40                  45

Gly Leu Lys Ser Val Ala Met Arg Gln Leu Ala Ile His Ala Ile Arg
    50                  55                  60

Glu Ala Gly Glu Lys His Ala Arg Glu Leu Ala Glu Leu Ala Val Ser
65                  70                  75                  80

Glu Thr Gly Met Gly Arg Val Asp Asp Lys Phe Ala Lys Asn Val Ala
                85                  90                  95
```

```
Gln Ala Arg Gly Thr Pro Gly Val Glu Cys Leu Ser Pro Gln Val Leu
            100                 105                 110
Thr Gly Asp Asn Gly Leu Thr Leu Ile Glu Asn Ala Pro Trp Gly Val
        115                 120                 125
Val Ala Ser Val Thr Pro Ser Thr Asn Pro Ala Ala Thr Val Ile Asn
    130                 135                 140
Asn Ala Ile Ser Leu Ile Ala Ala Gly Asn Ser Val Val Phe Ala Pro
145                 150                 155                 160
His Pro Ala Ala Lys Lys Val Ser Gln Arg Ala Ile Thr Leu Leu Asn
                165                 170                 175
Gln Ala Val Val Ala Ala Gly Pro Glu Asn Leu Leu Val Thr Val
            180                 185                 190
Ala Asn Pro Asp Ile Glu Thr Ala Gln Arg Leu Phe Lys Tyr Pro Gly
        195                 200                 205
Ile Gly Leu Leu Val Val Thr Gly Gly Glu Ala Val Val Asp Ala Ala
    210                 215                 220
Arg Lys His Thr Asn Lys Arg Leu Ile Ala Ala Gly Ala Gly Asn Pro
225                 230                 235                 240
Pro Val Val Val Asp Glu Thr Ala Asp Leu Pro Arg Ala Ala Gln Ser
                245                 250                 255
Ile Val Lys Gly Ala Ser Phe Asp Asn Asn Ile Ile Cys Ala Asp Glu
            260                 265                 270
Lys Val Leu Ile Val Val Asp Ser Val Ala Asp Glu Leu Met Arg Leu
        275                 280                 285
Met Glu Gly Gln His Ala Val Lys Leu Thr Ala Ala Gln Ala Glu Gln
    290                 295                 300
Leu Gln Pro Val Leu Leu Lys Asn Ile Asp Glu Arg Gly Lys Gly Thr
305                 310                 315                 320
Val Ser Arg Asp Trp Val Gly Arg Asp Ala Gly Lys Ile Ala Ala Ala
                325                 330                 335
Ile Gly Leu Asn Val Pro Asp Gln Thr Arg Leu Leu Phe Val Glu Thr
            340                 345                 350
Pro Ala Asn His Pro Phe Ala Val Thr Glu Met Met Met Pro Val Leu
        355                 360                 365
Pro Val Val Arg Val Ala Asn Val Glu Glu Ala Ile Ala Leu Ala Val
    370                 375                 380
Gln Leu Glu Gly Gly Cys His His Thr Ala Ala Met His Ser Arg Asn
385                 390                 395                 400
Ile Asp Asn Met Asn Gln Met Ala Asn Ala Ile Asp Thr Ser Ile Phe
                405                 410                 415
Val Lys Asn Gly Pro Cys Ile Ala Gly Leu Gly Leu Gly Gly Glu Gly
            420                 425                 430
Trp Thr Thr Met Thr Ile Thr Thr Pro Thr Gly Glu Gly Val Thr Ser
        435                 440                 445
Ala Arg Thr Phe Val Arg Leu Arg Arg Cys Val Leu Val Asp Ala Phe
    450                 455                 460
Arg Ile Val
465

<210> SEQ ID NO 7
<211> LENGTH: 467
<212> TYPE: PRT
<213> ORGANISM: Escherichia coli DH1

<400> SEQUENCE: 7
```

```
Met Asn Gln Gln Asp Ile Glu Gln Val Val Lys Ala Val Leu Leu Lys
1               5                   10                  15
Met Gln Ser Ser Asp Thr Pro Ser Ala Ala Val His Glu Met Gly Val
            20                  25                  30
Phe Ala Ser Leu Asp Asp Ala Val Ala Ala Lys Val Ala Gln Gln
        35                  40                  45
Gly Leu Lys Ser Val Ala Met Arg Gln Leu Ala Ile Ala Ala Ile Arg
    50                  55                  60
Glu Ala Gly Glu Lys His Ala Arg Asp Leu Ala Glu Leu Ala Val Ser
65                  70                  75                  80
Glu Thr Gly Met Gly Arg Val Glu Asp Lys Phe Ala Lys Asn Val Ala
            85                  90                  95
Gln Ala Arg Gly Thr Pro Gly Val Glu Cys Leu Ser Pro Gln Val Leu
            100                 105                 110
Thr Gly Asp Asn Gly Leu Thr Leu Ile Glu Asn Ala Pro Trp Gly Val
        115                 120                 125
Val Ala Ser Val Thr Pro Ser Thr Asn Pro Ala Ala Thr Val Ile Asn
        130                 135                 140
Asn Ala Ile Ser Leu Ile Ala Ala Gly Asn Ser Val Ile Phe Ala Pro
145                 150                 155                 160
His Pro Ala Ala Lys Lys Val Ser Gln Arg Ala Ile Thr Leu Leu Asn
            165                 170                 175
Gln Ala Ile Val Ala Ala Gly Gly Pro Glu Asn Leu Leu Val Thr Val
            180                 185                 190
Ala Asn Pro Asp Ile Glu Thr Ala Gln Arg Leu Phe Lys Phe Pro Gly
        195                 200                 205
Ile Gly Leu Leu Val Val Thr Gly Gly Glu Ala Val Val Glu Ala Ala
    210                 215                 220
Arg Lys His Thr Asn Lys Arg Leu Ile Ala Ala Gly Ala Gly Asn Pro
225                 230                 235                 240
Pro Val Val Val Asp Glu Thr Ala Asp Leu Ala Arg Ala Ala Gln Ser
            245                 250                 255
Ile Val Lys Gly Ala Ser Phe Asp Asn Asn Ile Ile Cys Ala Asp Glu
            260                 265                 270
Lys Val Leu Ile Val Val Asp Ser Val Ala Asp Glu Leu Met Arg Leu
        275                 280                 285
Met Glu Gly Gln His Ala Val Lys Leu Thr Ala Glu Gln Ala Gln Gln
290                 295                 300
Leu Gln Pro Val Leu Leu Lys Asn Ile Asp Glu Arg Gly Lys Gly Thr
305                 310                 315                 320
Val Ser Arg Asp Trp Val Gly Arg Asp Ala Gly Lys Ile Ala Ala Ala
            325                 330                 335
Ile Gly Leu Lys Val Pro Gln Glu Thr Arg Leu Leu Phe Val Glu Thr
        340                 345                 350
Thr Ala Glu His Pro Phe Ala Val Thr Glu Leu Met Met Pro Val Leu
        355                 360                 365
Pro Val Val Arg Val Ala Asn Val Ala Asp Ala Ile Ala Leu Ala Val
        370                 375                 380
Lys Leu Glu Gly Gly Cys His His Thr Ala Ala Met His Ser Arg Asn
385                 390                 395                 400
Ile Glu Asn Met Asn Gln Met Ala Asn Ala Ile Asp Thr Ser Ile Phe
            405                 410                 415
```

-continued

```
Val Lys Asn Gly Pro Cys Ile Ala Gly Leu Gly Leu Gly Gly Glu Gly
                420                 425                 430

Trp Thr Thr Met Thr Ile Thr Thr Pro Thr Gly Glu Gly Val Thr Ser
            435                 440                 445

Ala Arg Thr Phe Val Arg Leu Arg Arg Cys Val Leu Val Asp Ala Phe
        450                 455                 460

Arg Ile Val
465

<210> SEQ ID NO 8
<211> LENGTH: 467
<212> TYPE: PRT
<213> ORGANISM: Escherichia coli O104 H4 2009EL-2050

<400> SEQUENCE: 8

Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
            20                  25                  30

Phe Ala Ser Leu Asp Asp Ala Val Ala Ala Lys Val Ala Gln Gln
        35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320
```

Val Ser Arg Asp Trp Val Gly Arg Asp Ala Ala Lys Ile Ala Ala Ala
            325                 330                 335

Ile Gly Leu Asn Val Pro Gln Glu Thr Arg Leu Leu Phe Val Glu Thr
            340                 345                 350

Thr Ala Glu His Pro Phe Ala Val Thr Glu Leu Met Met Pro Val Leu
            355                 360                 365

Pro Val Val Arg Val Ala Asn Val Ala Asp Ala Ile Ala Leu Ala Val
            370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
            405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
            435                 440                 445

Ala Arg Thr Phe Val Arg Leu Arg Arg Cys Val Leu Val Asp Ala Phe
            450                 455                 460

Arg Ile Val
465

<210> SEQ ID NO 9
<211> LENGTH: 459
<212> TYPE: PRT
<213> ORGANISM: Dickeya dadantii 3937

<400> SEQUENCE: 9

Met Glu His Pro Val Ile Glu Pro Thr Val Pro Met Pro Ala Pro Val
1               5                   10                  15

Ile Phe Asp Ala Pro Ser Gly Ile Phe Asp Ser Leu Asp Asp Ala Val
            20                  25                  30

Gln Ala Ala Ala Gln Ala Gln Gln Gln Leu Thr Ser Val Glu Leu Arg
            35                  40                  45

Gln Gln Val Ile Lys Ala Ile Arg Val Ala Gly Glu Arg Tyr Ala Gln
        50                  55                  60

Val Leu Ala Glu Met Ala Val Ala Glu Thr Gly Met Gly Arg Val Val
65                  70                  75                  80

Asp Lys Tyr Val Lys Asn Val Ser Gln Ala Arg His Thr Pro Gly Ile
                85                  90                  95

Glu Cys Leu Ser Ala Glu Val Leu Thr Gly Asp Asn Gly Leu Thr Leu
            100                 105                 110

Ile Glu Asn Ala Pro Trp Gly Val Val Ala Ser Val Thr Pro Ser Thr
            115                 120                 125

Asn Pro Ala Ala Thr Val Ile Asn Asn Ala Ile Ser Met Ile Ala Ala
        130                 135                 140

Gly Asn Ser Val Val Phe Ala Pro His Pro Ser Ala Lys Lys Val Ser
145                 150                 155                 160

Leu Arg Thr Ile Ser Leu Leu Asn Lys Ala Ile Val Ala Thr Gly Gly
                165                 170                 175

Pro Glu Asn Leu Leu Val Ser Val Ala Asp Pro Asn Ile Glu Thr Ala
            180                 185                 190

Gln Arg Leu Phe Arg Tyr Pro Gly Ile Gly Leu Leu Val Val Thr Gly
            195                 200                 205

Gly Glu Ala Val Val Glu Ala Ala Arg Lys His Thr Asp Lys Arg Leu

```
                    210                 215                 220
Ile Ala Gly Ala Gly Asn Pro Val Val Asp Glu Thr Ala
225                 230                 235                 240

Asp Leu Pro Lys Ala Ala Arg Ala Ile Val Lys Gly Ala Ser Phe Asp
                245                 250                 255

Asn Asn Ile Ile Cys Ala Asp Glu Lys Val Leu Ile Val Val Asp Ser
                260                 265                 270

Val Ala Asp Ala Leu Leu Ala Glu Met Gln Arg Asn His Ala Val Leu
            275                 280                 285

Leu Thr Pro Glu Gln Thr Glu Arg Leu Leu Pro Ala Leu Leu Ser Asp
        290                 295                 300

Ile Asp Ala Gln Gly Lys Gly Arg Val Asn Arg Asp Tyr Val Gly Arg
305                 310                 315                 320

Asp Ala Ala Lys Leu Ala Ala Ile Gly Leu Glu Val Asn Glu His
                325                 330                 335

Thr Arg Leu Leu Leu Ala Glu Thr Asp Ala Gly His Pro Phe Ala Val
                340                 345                 350

Thr Glu Leu Met Met Pro Val Leu Pro Val Val Arg Val Lys Asn Val
            355                 360                 365

Asp Asp Ala Ile Ala Leu Ala Val Lys Leu Glu Asn Gly Cys Arg His
        370                 375                 380

Thr Ala Ala Met His Ser Thr Asn Ile Arg Asn Leu Asn Arg Met Ala
385                 390                 395                 400

Asn Ala Ile Asn Thr Ser Ile Phe Val Lys Asn Gly Pro Cys Ile Ala
                405                 410                 415

Gly Leu Gly Leu Gly Gly Glu Gly Trp Thr Ser Met Thr Ile Ser Thr
                420                 425                 430

Pro Thr Gly Glu Gly Val Thr Ser Ala Arg Thr Phe Val Arg Leu Arg
            435                 440                 445

Arg Cys Val Leu Val Asp Met Phe Arg Ile Ala
        450                 455

<210> SEQ ID NO 10
<211> LENGTH: 459
<212> TYPE: PRT
<213> ORGANISM: Dickeya zeae

<400> SEQUENCE: 10

Met Glu His Ser Val Ile Glu Pro Thr Val Pro Met Pro Leu Pro Ala
1               5                   10                  15

Met Phe Asp Ala Pro Ser Gly Ile Phe Ser Ser Leu Asp Asp Ala Val
                20                  25                  30

Gln Ala Ala Thr Leu Ala Gln Gln Gln Leu Ser Ser Val Glu Leu Arg
            35                  40                  45

Gln Gln Val Ile Lys Ala Ile Arg Val Ala Gly Glu Arg Tyr Ala Gln
        50                  55                  60

Val Leu Ala Glu Met Ala Val Ala Glu Thr Gly Met Gly Arg Val Val
65                  70                  75                  80

Asp Lys Tyr Ile Lys Asn Val Ser Gln Ala Arg His Thr Pro Gly Ile
                85                  90                  95

Glu Cys Leu Ser Ala Glu Val Leu Thr Gly Asp Asn Gly Leu Thr Leu
            100                 105                 110

Ile Glu Asn Ala Pro Trp Gly Val Val Ala Ser Val Thr Pro Ser Thr
        115                 120                 125
```

```
Asn Pro Ala Ala Thr Val Ile Asn Asn Ala Ile Ser Met Ile Ala Ala
            130                 135                 140

Gly Asn Ser Val Val Phe Ala Pro His Pro Ser Ala Lys Asn Val Ser
145                 150                 155                 160

Leu Arg Thr Ile Ser Leu Leu Asn Lys Ala Ile Val Ala Thr Gly Gly
                165                 170                 175

Pro Glu Asn Leu Leu Val Ser Val Ala Asn Pro Asn Ile Glu Thr Ala
            180                 185                 190

Gln Arg Leu Phe Arg Tyr Pro Gly Ile Gly Leu Leu Val Thr Gly
            195                 200                 205

Gly Glu Ala Val Val Glu Ala Ala Arg Lys His Thr Asp Lys Arg Leu
210                 215                 220

Ile Ala Ala Gly Ala Gly Asn Pro Pro Val Val Asp Glu Thr Ala
225                 230                 235                 240

Asp Ile Pro Lys Ala Ala Arg Ala Ile Val Lys Gly Ala Ser Phe Asp
                245                 250                 255

Asn Asn Ile Ile Cys Ala Asp Glu Lys Val Leu Ile Val Val Asp Arg
                260                 265                 270

Val Ala Asp Ala Leu Leu Ala Glu Met Gln Arg Asn Asn Ala Val Leu
            275                 280                 285

Leu Thr Pro Glu Gln Thr Glu Arg Leu Leu Pro Ala Leu Leu Ser Asp
290                 295                 300

Ile Asp Glu Gln Gly Lys Gly Arg Val Asn Arg Asp Tyr Val Gly Arg
305                 310                 315                 320

Asp Ala Ala Lys Leu Ala Ala Ala Ile Gly Leu Glu Val Ser Glu His
                325                 330                 335

Thr Arg Leu Leu Leu Ala Glu Thr Asp Ala Asp His Pro Phe Ala Val
            340                 345                 350

Thr Glu Leu Met Met Pro Val Leu Pro Val Ile Arg Val Lys Asn Val
            355                 360                 365

Asp Asp Ala Ile Ala Leu Ala Val Lys Leu Glu Ser Gly Cys Arg His
            370                 375                 380

Thr Ala Ala Met His Ser Thr Asn Ile Arg Asn Leu Asn Arg Met Ala
385                 390                 395                 400

Asn Ala Ile Asn Thr Ser Ile Phe Val Lys Asn Gly Pro Cys Ile Ala
                405                 410                 415

Gly Leu Gly Leu Gly Gly Glu Gly Trp Thr Ser Met Thr Ile Ser Thr
            420                 425                 430

Pro Thr Gly Glu Gly Val Thr Ser Ala Arg Thr Phe Val Arg Leu Arg
            435                 440                 445

Arg Cys Val Leu Val Asp Met Phe Arg Ile Ala
    450                 455

<210> SEQ ID NO 11
<211> LENGTH: 478
<212> TYPE: PRT
<213> ORGANISM: Morganella morganii

<400> SEQUENCE: 11

Met Asp Gln Lys Glu Ile Glu Asn Val Val Lys Ala Val Leu Ala Ser
1               5                   10                  15

Met Ser Ala Gly Thr Gln Pro Ala Ala Ser Ala Ala Pro Gln Gln
            20                  25                  30

Ala Ala Ala Ser Gln Asn Asn Gly Phe Gly Val Phe Glu Ser Leu Asp
            35                  40                  45
```

```
Asp Ala Val Leu Ala Ala Lys Glu Ala Gln Lys Ser Leu Lys Thr Val
    50                  55                  60

Glu Met Arg Asn Leu Cys Ile Gly Ala Ile Arg Ala Ala Thr Glu
65                  70                  75                  80

His Ala Arg Glu Leu Ala Val Leu Ala Val Glu Glu Thr Gly Met Gly
                    85                  90                  95

Arg Val Glu Asp Lys Leu Ala Lys Asn Leu Ala Gln Ala Asn Gly Thr
                100                 105                 110

Pro Gly Val Glu Cys Leu Arg Pro Glu Val Leu Thr Gly Asp His Gly
            115                 120                 125

Leu Thr Leu Ile Glu Asn Ala Ala Trp Gly Val Ile Ala Ser Val Thr
        130                 135                 140

Pro Ser Thr Asn Pro Ala Ala Thr Ala Ile Asn Asn Ala Ile Ser Met
145                 150                 155                 160

Ile Ala Gly Gly Asn Ser Val Ile Phe Ala Pro His Pro Ala Ala Lys
                165                 170                 175

Lys Val Ser Gln Arg Thr Ile Thr Ile Leu Asn Glu Ala Ile Val Ala
                180                 185                 190

Ala Gly Gly Pro Asn Asn Leu Leu Val Thr Val Ala Lys Pro Asp Ile
        195                 200                 205

Glu Thr Ala Gln Arg Leu Phe Lys Tyr Pro Gly Ile Gly Leu Leu Val
    210                 215                 220

Val Thr Gly Gly Asp Ala Val Val Glu Ser Ala Arg Lys His Thr Asn
225                 230                 235                 240

Lys Arg Leu Ile Ala Ala Gly Ala Gly Asn Pro Pro Val Val Val Asp
                245                 250                 255

Glu Thr Ala Asp Ile Glu Arg Ala Ala Lys Ala Ile Val His Gly Ala
                260                 265                 270

Ser Phe Asp Asn Asn Ile Ile Cys Ala Asp Glu Lys Val Leu Ile Ala
        275                 280                 285

Val Asp Cys Ile Ala Asp Lys Leu Ile Thr Glu Met Gln Arg Asn His
    290                 295                 300

Ala Val Leu Leu Thr Arg Glu Gln Ser Glu Lys Leu Ile Pro Val Leu
305                 310                 315                 320

Leu Lys Asn Val Asp Glu Thr Gly His Gly Thr Val Ser Arg Asp Trp
                325                 330                 335

Val Gly Arg Asp Ala Ala Lys Ile Ala Ala Ile Gly Met Thr Val
                340                 345                 350

Pro Ala Asp Thr Arg Leu Leu Ile Ala Glu Thr Asp Cys Lys His Pro
        355                 360                 365

Phe Ala Val Thr Glu Leu Met Met Pro Val Leu Pro Ile Ile Arg Val
    370                 375                 380

Lys Asp Val Asp Gln Ala Ile Asp Leu Ala Val Lys Leu Glu Gly Gly
385                 390                 395                 400

Cys His His Thr Ala Ala Met His Ser Asn Asn Ile Ser Asn Leu Asn
                405                 410                 415

Arg Met Ala Asn Ala Ile Asp Thr Ser Ile Phe Val Lys Asn Gly Pro
                420                 425                 430

Cys Ile Ala Gly Leu Gly Leu Gly Gly Glu Gly Trp Thr Thr Met Thr
        435                 440                 445

Ile Thr Thr Pro Thr Gly Glu Gly Val Thr Cys Ala Arg Thr Phe Val
    450                 455                 460
```

```
Arg Leu Arg Arg Cys Thr Met Val Asp Ser Phe Arg Ile Val
465                 470                 475
```

<210> SEQ ID NO 12
<211> LENGTH: 23
<212> TYPE: DNA
<213> ORGANISM: Artificial Sequence
<220> FEATURE:
<223> OTHER INFORMATION: Synthetic DNA

<400> SEQUENCE: 12

```
cgcgccatat gaatcaacag gac                                              23
```

<210> SEQ ID NO 13
<211> LENGTH: 24
<212> TYPE: DNA
<213> ORGANISM: Artificial Sequence
<220> FEATURE:
<223> OTHER INFORMATION: Synthetic DNA

<400> SEQUENCE: 13

```
tacgattcga aacgcatcca ccag                                             24
```

<210> SEQ ID NO 14
<211> LENGTH: 699
<212> TYPE: DNA
<213> ORGANISM: Nostoc punctiform
<220> FEATURE:
<221> NAME/KEY: CDS
<222> LOCATION: (1)..(699)

<400> SEQUENCE: 14

```
atg cag cag ctt aca gac caa tct aaa gaa tta gat ttc aag agc gaa        48
Met Gln Gln Leu Thr Asp Gln Ser Lys Glu Leu Asp Phe Lys Ser Glu
1               5                   10                  15 aca tac aaa gat gct tat agc cgg att aat gcg atc gtg att gaa ggg        96
Thr Tyr Lys Asp Ala Tyr Ser Arg Ile Asn Ala Ile Val Ile Glu Gly
                20                  25                  30 gaa caa gaa gcc cat gaa aat tac atc aca cta gcc caa ctg ctg cca       144
Glu Gln Glu Ala His Glu Asn Tyr Ile Thr Leu Ala Gln Leu Leu Pro
            35                  40                  45 gaa tct cat gat gaa ttg att cgc cta tcc aag atg gaa agc cgc cat       192
Glu Ser His Asp Glu Leu Ile Arg Leu Ser Lys Met Glu Ser Arg His
        50                  55                  60 aag aaa gga ttt gaa gct tgt ggg cgc aat tta gct gtt acc cca gat       240
Lys Lys Gly Phe Glu Ala Cys Gly Arg Asn Leu Ala Val Thr Pro Asp
65                  70                  75                  80 ttg caa ttt gcc aaa gag ttt ttc tcc ggc cta cac caa aat ttt caa       288
Leu Gln Phe Ala Lys Glu Phe Phe Ser Gly Leu His Gln Asn Phe Gln
                85                  90                  95 aca gct gcc gca gaa ggg aaa gtg gtt act tgt ctg ttg att cag tct       336
Thr Ala Ala Ala Glu Gly Lys Val Val Thr Cys Leu Leu Ile Gln Ser
            100                 105                 110 tta att att gaa tgt ttt gcg atc gca gca tat aac att tac atc ccc       384
Leu Ile Ile Glu Cys Phe Ala Ile Ala Ala Tyr Asn Ile Tyr Ile Pro
        115                 120                 125 gtt gcc gac gat ttc gcc cgt aaa att act gaa gga gta gtt aaa gaa       432
Val Ala Asp Asp Phe Ala Arg Lys Ile Thr Glu Gly Val Val Lys Glu
    130                 135                 140 gaa tac agc cac ctc aat ttt gga gaa gtt tgg ttg aaa gaa cac ttt       480
Glu Tyr Ser His Leu Asn Phe Gly Glu Val Trp Leu Lys Glu His Phe
145                 150                 155                 160 gca gaa tcc aaa gct gaa ctt gaa ctt gca aat cgc cag aac cta ccc       528
Ala Glu Ser Lys Ala Glu Leu Glu Leu Ala Asn Arg Gln Asn Leu Pro
```

```
Ala Glu Ser Lys Ala Glu Leu Glu Leu Ala Asn Arg Gln Asn Leu Pro
                165                 170                 175 atc gtc tgg aaa atg ctc aac caa gta gaa ggt gat gcc cac aca atg    576
Ile Val Trp Lys Met Leu Asn Gln Val Glu Gly Asp Ala His Thr Met
        180                 185                 190 gca atg gaa aaa gat gct ttg gta gaa gac ttc atg att cag tat ggt    624
Ala Met Glu Lys Asp Ala Leu Val Glu Asp Phe Met Ile Gln Tyr Gly
    195                 200                 205 gaa gca ttg agt aac att ggt ttt tcg act cgc gat att atg cgc ttg    672
Glu Ala Leu Ser Asn Ile Gly Phe Ser Thr Arg Asp Ile Met Arg Leu
210                 215                 220 tca gcc tac gga ctc ata ggt gct taa                                699
Ser Ala Tyr Gly Leu Ile Gly Ala
225                 230
```

<210> SEQ ID NO 15
<211> LENGTH: 232
<212> TYPE: PRT
<213> ORGANISM: Nostoc punctiform

<400> SEQUENCE: 15

```
Met Gln Gln Leu Thr Asp Gln Ser Lys Glu Leu Asp Phe Lys Ser Glu
1               5                   10                  15

Thr Tyr Lys Asp Ala Tyr Ser Arg Ile Asn Ala Ile Val Ile Glu Gly
                20                  25                  30

Glu Gln Glu Ala His Glu Asn Tyr Ile Thr Leu Ala Gln Leu Leu Pro
            35                  40                  45

Glu Ser His Asp Glu Leu Ile Arg Leu Ser Lys Met Glu Ser Arg His
        50                  55                  60

Lys Lys Gly Phe Glu Ala Cys Gly Arg Asn Leu Ala Val Thr Pro Asp
65                  70                  75                  80

Leu Gln Phe Ala Lys Glu Phe Phe Ser Gly Leu His Gln Asn Phe Gln
                85                  90                  95

Thr Ala Ala Ala Glu Gly Lys Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
130                 135                 140

Glu Tyr Ser His Leu Asn Phe Gly Glu Val Trp Leu Lys Glu His Phe
145                 150                 155                 160

Ala Glu Ser Lys Ala Glu Leu Glu Leu Ala Asn Arg Gln Asn Leu Pro
                165                 170                 175

Ile Val Trp Lys Met Leu Asn Gln Val Glu Gly Asp Ala His Thr Met
            180                 185                 190

Ala Met Glu Lys Asp Ala Leu Val Glu Asp Phe Met Ile Gln Tyr Gly
        195                 200                 205

Glu Ala Leu Ser Asn Ile Gly Phe Ser Thr Arg Asp Ile Met Arg Leu
    210                 215                 220

Ser Ala Tyr Gly Leu Ile Gly Ala
225                 230
```

<210> SEQ ID NO 16
<211> LENGTH: 133
<212> TYPE: DNA
<213> ORGANISM: Artificial Sequence
<220> FEATURE:
<223> OTHER INFORMATION: Synthetic DNA

```
<400> SEQUENCE: 16
taccatgggc atacatatgg ccatcataac ggttctggca aatattctga aatgagctgt      60
tgacaattaa tcatcggctc gtataatgtg tggaattgtg agcggataac aatttcacac     120
aaggagatat acg                                                        133

<210> SEQ ID NO 17
<211> LENGTH: 113
<212> TYPE: DNA
<213> ORGANISM: Artificial Sequence
<220> FEATURE:
<223> OTHER INFORMATION: Synthetic DNA

<400> SEQUENCE: 17
taattaacct aggctgctgc caccgctgag caataactag cataacccct tggggcctct      60
aaacgggtct tgagggttt tttgccctcg agtccggccg catgcggccg cat             113
```

RECOMBINANT MICROORGANISM AND METHOD FOR PRODUCING A SUBSTANCE USING THE SAME

TECHNICAL FIELD

The present invention relates to a recombinant microorganism into which a gene associated with production of a target substance has been introduced and a method for producing a substance using such recombinant microorganism.

BACKGROUND ART

Microorganisms capable of synthesizing an aldehyde, an alcohol, or a hydrocarbon, such as alkane, alkene, or alkyne, have been known. JP 2011-520455 A discloses an alkane synthase gene and an aldehyde synthase gene derived from *Synechococcus elongatus*, and it also discloses a method for producing an alkane or an aldehyde using such genes.

JP 2002-223788 A discloses the production of an alcohol using a transformed plant into which the acyl reductase gene has been introduced and, as a substrate, an aliphatic-acyl group bound to CoA and/or ACP. While JP 2002-223788 A describes that the acyl reductase gene is isolated from green algae, it does not disclose that a transformed plant is actually produced.

Further, JP 2013-528057 A discloses that aliphatic acyl-CoA reductase derived from *Clostridium kluyveri* is prepared and transformed into an *E. coli* strain together with another lipid synthesis-associated gene.

Furthermore, JP 2012-506715 A discloses a method for producing an aliphatic alcohol comprising expressing a gene encoding an aliphatic aldehyde biosynthetic polypeptide that reduces carboxylic acid into an aldehyde or a variant thereof in a host, so as to synthesize an aliphatic aldehyde, and producing an alcohol from an aliphatic aldehyde.

In addition, JP 2011-512848 A discloses a method for genetically engineering microorganisms capable of producing a primary alcohol using a malonyl-CoA-independent FAS metabolic pathway and an acyl reduction metabolic pathway.

Further, JP 2010-528627 A discloses a method for producing an oil component by introducing genes associated with oil and fat production into microalgae of *Chlorella*.

JP 2012-511928 A discloses microorganisms into which nucleic acids encoding isopropanol pathway enzymes such as succinyl-CoA:3-ketoacid-CoA transferase have been introduced and a method for producing isopropanol using such microorganisms.

SUMMARY OF THE INVENTION

Objects to Be Attained by the Invention

There have been no acyl-CoA reductases known to exert excellent activity in microorganisms, and productivity has been disadvantageously low regarding an aldehyde generated via reduction from aliphatic acyl-CoA as a substrate or an alcohol or a hydrocarbon generated from such an aldehyde as a substrate.

Under the above circumstances, it is an object of the present invention to provide a recombinant microorganism into which an acyl-CoA reductase exerting excellent activity in a reduction reaction using acyl-CoA as a substrate has been introduced, and it is another object of the present invention to provide a method for producing a substance using such recombinant microorganism.

Means for Attaining the Objects

The present inventors have conducted concentrated studies in order to attain the above objects. As a result, they discovered that a particular type of aldehyde dehydrogenase has activity of synthesizing an aldehyde compound from acyl-CoA. This has led to the completion of the present invention.

(1) A recombinant microorganism comprising a nucleic acid encoding a protein (a) or (b) below introduced into a host microorganism:
 (a) a protein comprising the amino acid sequence of SEQ ID NO: 2; or
 (b) a protein comprising an amino acid sequence having 70% or higher identity to the amino acid sequence of SEQ ID NO: 2 and having activity for synthesizing an aldehyde compound from acyl-CoA.
(2) The recombinant microorganism according to (1), wherein the host microorganism is selected from the group consisting of *Escherichia coli, Corynebacterium*, and yeast.
(3) The recombinant microorganism according to (1), which has aldehyde decarbonylase activity for synthesizing a hydrocarbon using an aldehyde as a substrate.
(4) The recombinant microorganism according to (1), wherein the host microorganism has a nucleic acid encoding an aldehyde decarbonylase that synthesizes a hydrocarbon using an aldehyde as a substrate.
(5) The recombinant microorganism according to (1), which produces a hydrocarbon comprising a carbon chain of 13 to 15 carbon atoms.
(6) A method for producing a substance comprising a step of culturing the recombinant microorganism according to any of (1) to (5) in a medium containing a carbon source and a step of recovering a target substance from the cultured recombinant microorganism.
(7) The method for producing a substance according to (6), wherein the target substance is at least one member selected from the group consisting of an aliphatic aldehyde, an aliphatic alcohol, and a hydrocarbon.

Effects of the Invention

The recombinant microorganism according to the present invention expresses an acyl-CoA reductase that exerts excellent activity in a reduction reaction from an aliphatic acyl-CoA as a substrate. Accordingly, such recombinant microorganism is excellent in terms of productivity of an aliphatic aldehyde caused by reduction of an aliphatic acyl-CoA with the aid of the acyl-CoA reductase, an aliphatic alcohol converted from the aliphatic aldehyde, and a hydrocarbon.

According to the method for producing a substance of the present invention, a recombinant microorganism that is excellent in terms of productivity of an aliphatic aldehyde caused by reduction of an aliphatic acyl-CoA with the aid of the acyl-CoA reductase, an aliphatic alcohol converted from the aliphatic aldehyde, and a hydrocarbon is used. Thus, productivity of substances, including an aliphatic aldehyde, an aliphatic alcohol, and a hydrocarbon, can be remarkably improved.

EMBODIMENTS FOR CARRYING OUT THE INVENTION

Figure 1:
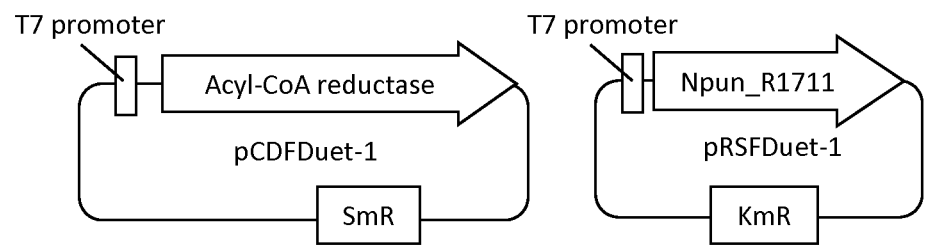
FIG. 1 schematically shows constitutions of the two expression vectors (pCDFDuet-1 and pRSFDuet-1) prepared in examples.

Hereafter, the present invention is described in more detail with reference to the drawings and the examples.

The recombinant microorganism according to the present invention comprises a nucleic acid encoding a particular acyl-CoA reductase introduced thereinto. The recombinant microorganism according to the present invention expresses the acyl-CoA reductase to thereby reduce acyl-CoA (it is occasionally referred to as "aliphatic acyl-CoA"), which is a thioester compound of an aliphatic acid with CoA, and produce an aldehyde compound with high efficiency. The aldehyde compound produced is oxidized in the metabolic reaction within the microorganism and converted into an alcohol, or it is used as a substrate for hydrocarbon synthesis by an enzyme having hydrocarbon-synthesizing activity. Thus, the recombinant microorganism according to the present invention is not only capable of producing an aldehyde with high efficiency, but it is also capable of producing an alcohol and/or hydrocarbon from such aldehyde compound with high efficiency, through expression of the acyl-CoA reductase.

The term "nucleic acid" refers to a nucleic acid existing in nature, such as DNA or RNA, or an artificial nucleic acid, such as a nucleic acid molecule resulting from chemical modification to PNA (peptide nucleic acid), a nucleotide, a sugar, or a diester phosphate moiety. The term "a nucleic acid encoding an acyl-CoA reductase" refers both to a region comprising an expression regulatory region and a coding region in the genome and a region consisting of a coding region in the genome.

Acyl-CoA is synthesized from a sugar as a result of the metabolic reaction in a host microorganism. A sugar is a substance represented by a chemical formula $C_n(H_2O)_m$. Examples thereof include an aldehyde of a polyhydric alcohol, a ketone derivative of a polyhydric alcohol, and derivatives and condensates of substances related thereto, and specific examples include polysaccharides, oligosaccharides, disaccharides, and monosaccharides. Specific examples of monosaccharides include glucose, fructose, galactose, mannose, xylose, xylulose, ribose, erythrose, threose, erythrulose, glyceraldehyde, and dihydroxyacetone. Specific examples of disaccharides include sucrose (saccharose), lactose, maltose, trehalose, and cellobiose.

[Acyl-CoA Reductase]

With regard to the recombinant microorganism of the present invention, a nucleic acid encoding a particular acyl-CoA reductase is, for example, a nucleic acid encoding a protein comprising the amino acid sequence of SEQ ID NO: 2. The amino acid sequence of SEQ ID NO: 2 can be identified as a sequence similar to that of a known aldehyde dehydrogenase (AldDH) via genomic analysis of Klebsiella pneumoniae subsp. pneumoniae NBRC3321. However, functions and other properties of the protein comprising the amino acid sequence of SEQ ID NO: 2 remain unknown.

A nucleic acid encoding a particular acyl-CoA reductase may encode a protein comprising an amino acid sequence that is different from the amino acid sequence of SEQ ID NO: 2 and having activity of an acyl-CoA reductase.

For example, a nucleic acid encoding a particular type of acyl-CoA reductase may encode a protein comprising an amino acid sequence derived from the amino acid sequence of SEQ ID NO: 2 by deletion, substitution, addition, or insertion of 1 or a plurality of amino acids and having activity of an acyl-CoA reductase. A plurality of amino acids is, for example, 1 to 20, preferably 1 to 10, more preferably 1 to 7, further preferably 1 to 5, and particularly preferably 1 to 3 amino acids. Amino acid deletion, substitution, or addition can be performed by modifying the nucleotide sequence of the nucleic acid encoding the acyl-CoA reductase in accordance with a technique known in the art. A mutation can be introduced into a nucleotide sequence by conventional techniques, such as the Kunkel method or the Gapped duplex method, or a technique in accordance therewith. For example, a site-directed mutagenesis kit (e.g., Mutant-K or Mutant-G (trade names); manufactured by TAKARA Bio) may be used. Alternatively, a mutation may be introduced using the LA PCR in vitro Mutagenesis Series Kit (trade name: manufactured by TAKARA Bio). Further, mutagenesis may be carried out with the use of a chemical mutagen. Representative examples of chemical mutagens include EMS (ethylmethane sulfonate), 5-bromouracil, 2-aminopurine, hydroxylamine, N-methyl-N'-nitro-N-nitrosoguanidine, and other carcinogenic compounds. Also, it may be carried out by radiation application and ultraviolet processing with the use of x rays, α rays, β rays, γ rays, or ion beams.

For example, a nucleic acid encoding a particular type of acyl-CoA reductase may encode a protein comprising an amino acid sequence having 70% or higher, preferably 75% or higher, more preferably 80% or higher, further preferably 90% or higher, still further preferably 95% or higher, and most preferably 99% or higher similarity or identity to the amino acid sequence of SEQ ID NO: 2 and having activity of an acyl-CoA reductase. The degree of similarity or identity is determined using a computer program equipped with the basic local alignment search tool (BLAST) program and a database storing gene sequence information by default.

More specifically, Table 1 shows the results of searching of the database storing protein amino acid sequences with the use of the so-called Blast Search Programs on the basis of the amino acid sequence of SEQ ID NO: 2.

TABLE 1

| Gene ID | Gene origin | SEQ ID NO |
|---|---|---|
| D364_14210 | Klebsiella pneumoniae CG43 | SEQ ID NO 3 |
| KPN2242_17010 | Klebsiella pneumoniae KCTC 2242 | SEQ ID NO 4 |
| CFSAN002069_19445 | Salmonella enterica subsp. enterica Serovar Heidelberg CFSAN002069 | SEQ ID NO 5 |
| SG2494 | Salmonella enterica subsp. enterica serovar Gallinarum 287/91 | SEQ ID NO 6 |
| EcDH1_1215 | Escherichia coli DH1 | SEQ ID NO 7 |
| O3M_07220 | Escherichia coli O104 H4 2009EL-2050 | SEQ ID NO 8 |
| Dda3937_03173 | Dickeya dadantii 3937 | SEQ ID NO 9 |
| Dd1591_0964 | Dickeya zeae | SEQ ID NO 10 |
| MU9_1040 | Morganella morganii | SEQ ID NO 11 |

As shown in Table 1, 9 types of genes can be identified as genes encoding proteins having 75% or higher homology to the amino acid sequence of SEQ ID NO: 2. Since these 9 types of genes show as high as 75% or higher homology to a protein comprising the amino acid sequence of SEQ ID NO: 2, these genes encode proteins having activity of an acyl-CoA reductase, as well as the protein comprising the amino acid sequence of SEQ ID NO: 2.

An example of a nucleic acid encoding a particular acyl-CoA reductase is a nucleic acid hybridizing under stringent conditions to a nucleic acid encoding the amino acid sequence of SEQ ID NOs: 2 (e.g., a nucleic acid comprising the nucleotide sequence of SEQ ID NO: 1) and encoding a protein having activity of an acyl-CoA reductase. Under stringent conditions, namely, a specific hybrid is formed, but a non-specific hybrid is not formed. For example, such conditions comprise hybridization at 45° C. with 6×SSC (sodium chloride/sodium citrate), followed by washing at 50° C. to 65° C. with 0.2 to 1×SSC and 0.1% SDS. Alternatively, such conditions comprise hybridization at 65° C. to 70° C. with 1×SSC, followed by washing at 65° C. to 70° C. with 0.3×SSC. Hybridization can be carried out by a conventional technique, such as the method described in J. Sambrook et al., Molecular Cloning: A Laboratory Manual, 2nd Ed., Cold Spring Harbor Laboratory, 1989.

Alternatively, a nucleic acid encoding a particular type of acyl-CoA reductase may encode a protein comprising, for example, an amino acid sequence derived from the amino acid sequence of SEQ ID NO: 2 by conservative amino acid substitution and having activity of an acyl-CoA reductase. The term "conservative amino acid substitution" used herein may be defined as follows. As described in Reference Document (1) (McKee Biochemistry, Third Edition, Chapter 5: Amino acids, Peptides, and Proteins, 5.1: Amino acids, Atsushi Ichikawa (supervising editor), Shinichi Fukuoka (supervising translator), Ryosuke Sone (publisher), Kagaku-Dojin Publishing Company, Inc., ISBN4-7598-0944-9), specifically, it is well known that amino acids are classified in accordance with side chains having similar properties (chemical properties or physical sizes). Also, it is well known that molecular evolutionary substitutions frequently occur between amino acid residues classified as members of a given group while maintaining protein activity. On the basis thereof, the amino acid substitution scoring matrix (BLOSUM) shown in FIG. 2 in Reference Document (2): Henikoff S., Henikoff J. G., Amino-acid substitution matrices from protein blocks, Proc. Natl. Acad. Sci. U.S.A., 89, 10915-10919, 1992 was proposed, and such technique has been extensively employed. Reference Document (2) is based on the finding such that substitution between amino acids having similar side-chain chemical properties would reduce changes in structures and functions occurring throughout a protein. According to Reference Documents (1) and (2), a group of side-chain amino acids to be taken into consideration for multiple alignment can be based on indicators such as chemical properties and physical sizes. According to the scoring matrix (BLOSUM) disclosed in Reference Document (2), such group of side-chain amino acids is indicated as a group of amino acids having a score of 0 or more, and preferably of 1 or more. Examples of representative groups include the 8 groups described below. Amino acids can be classified into more specific groups: for example, a group of amino acids having a score of 0 or more; a group of amino acids having a score of 1 or more; and a group of amino acids having a score of 2 or more.

1) Aliphatic Hydrophobic Amino Acids Group (ILMV Group)

This group consists of amino acids comprising aliphatic hydrophobic side chains among the neutral non-polar amino acids described in Reference Document (1); i.e., V (Val, valine), L (Leu, leucine), I (Ile, isoleucine), and M (Met, methionine). Among the amino acids that are classified as the neutral non-polar amino acids according to Reference Document (1), FGACWP are not included in "the group of hydrophobic aliphatic amino acids" for the following reasons. That is, the size of G (Gly, glycine) or A (Ala, alanine) is less than or equal to that of a methyl group, and the effects of non-polar amino acids are weak. Also, C (Cys, cysteine) occasionally plays a key role in S—S bonding, and it forms a hydrogen bond with an oxygen or nitrogen atom. In addition, the side chain molecular weights of F (Phe, phenylalanine) and W (Trp, tryptophane) are particularly high, and the effects of aromatic amino acids are strong. Further, P (Pro, proline) fixes the angle of the polypeptide main chain because of its strong imino acid effects.

2) Group of Amino Acids Having Hydroxymethylene Groups (ST Group)

This group consists of amino acids having hydroxymethylene groups in the side chains among the neutral polar amino acids; i.e., S (Ser, serine) and T (Thr, threonine). Since sugars bind at the sites of hydroxyl groups existing in the S and T side chains, such sites of hydroxyl groups are often important for a given type of polypeptide (protein) to have particular activity.

3) Group of Acidic Amino Acids (DE Group)

This group consists of amino acids having acidic carboxyl groups in the side chains; i.e., D (Asp, aspartic acid) and E (Glu, glutamic acid).

4) Group of Basic Amino acids (KR Group)

This group consists of basic amino acids; i.e., K (Lys, lysine) and R (Arg, arginine). K and R are positively charged over an extensive pH range and they have basic properties. In contrast, H (His, histidine), classified as a basic amino acid, is not substantially ionized at pH 7, and it is accordingly not classified as a member of this group.

5) Group of Amino Acids Comprising Methylene Group=Polar Group (DHN Group)

All amino acids classified as members of this group comprise methylene groups bound as side chains to carbon atoms at position cc and polar groups at sites closer to the ends thereof. The amino acids of this group are very similar in terms of physical sizes of non-polar methylene groups, and the group consists of N (Asn, asparagine, with the polar group being an amide group), D (Asp, aspartic acid, with the polar group being a carboxyl group), and H (His, histidine, with the polar group being an imidazole group).

6) Group of Amino Acids Comprising Dimethylene Group=Polar Group (EKQR Group)

All amino acids classified as members of this group comprise linear hydrocarbons equal to or larger than dimethylene groups bound as side chains to carbon atoms at position α and polar groups at sites closer to the ends thereof. The amino acids of this group are very similar in terms of physical sizes of non-polar dimethylene groups, and the group consists of E (Glu, glutamic acid, with the polar group being a carboxyl group), K (Lys, lysine, with the polar group being an amino group), Q (Gln, glutamine, with the polar group being an amide group), and R (Arg, arginine, with the polar groups being imino and amino groups).

7) Group of Aromatic Amino Acids (FYW Group)

This group consists of aromatic amino acids comprising benzene nuclei in the side chains and having chemical properties peculiar to aromatic amino acids: i.e., F (Phe, phenylalanine), Y (Tyr, tyrosine), and W (Trp, tryptophane).

8) Group of Cyclic Polar Amino Acids (HY Group)

This group consists of amino acids having both cyclic structures and polar groups in the side chains; i.e., H (H, histidine, with both the cyclic structure and the polar group being imidazole groups) and Y (Tyr, tyrosine, with the cyclic structure being a benzene nucleus and the polar group being a hydroxyl group).

On the basis of the groups of amino acids described above, it can be easily deduced that novel proteins having the same functions are obtained by substituting an amino acid residue in the amino acid sequence of a protein having a given function with another amino acid residue of the same group. On the basis of "1) Aliphatic hydrophobic amino acids group (ILMV group)" above, for example, it can be easily deduced that novel proteins having the same functions are obtained even if an isoleucine residue in the amino acid sequence of a protein having a particular function is substituted with a leucine residue. When there are a plurality of proteins having particular functions, amino acid sequences are occasionally described as consensus sequences. Even in such cases, it can be easily deduced that novel proteins having the same functions are obtained by substituting a particular amino acid residue with another amino acid residue of the same group. When there are a plurality of proteins having particular functions and the amino acid residue in the consensus sequence determined based thereon is isoleucine or leucine (L/I), for example, it can be easily deduced that novel proteins having the same functions are obtained even if the isoleucine or leucine residue is substituted with a methionine or valine residue on the basis of "1) Aliphatic hydrophobic amino acids group (ILMV group)."

Whether or not a nucleic acid comprising a particular nucleotide sequence encodes the acyl-CoA reductase can be determined by preparing an expression vector comprising the nucleic acid incorporated into a site between an adequate promoter and a terminator, transforming an adequate host using the prepared expression vector, and assaying the acyl-CoA reductase activity of the protein expressed. Acyl-CoA reductase activity can be assayed by culturing the transformant in a medium containing a carbon source and analyzing the synthesized aldehyde compound or an alcohol derived from the aldehyde compound via gas chromatography, mass analysis, or other means. When culturing the transformant, acyl-CoA may be added to the medium.

[Expression Vector and Host Microorganism]

The nucleic acid encoding the acyl-CoA reductase described above is incorporated into an adequate expression vector and it is then introduced into a host microorganism. A host microorganism is not particularly limited, provided that it is capable of expressing an acyl-CoA reductase. Examples of host microorganisms include: bacteria of *Escherichia* such as *Escherichia coli*, *Corynebacterium* such as *Corynebacterium glutamicum*, *Bacillus* such as *Bacillus subtilis*, *Pseudomonas* such as *Pseudomonas putida*, and *Rhizobium* such as *Rhizobium meliloti*; and fungi including yeast and filamentous fungi, such as *Saccharomyces cerevisiae*, *Schizosaccharomyces pombe*, and *Pichia pastoris*.

When bacteria such as *Escherichia coli* are used for host microorganisms, it is preferable that an expression vector be capable of autonomous replication in such bacteria and be composed of a promoter, a ribosome binding sequence, the gene(s) described above, and a transcription terminator sequence. Also, an expression vector may comprise a gene that regulates promoter activity.

Any *Escherichia coli* strains that have heretofore been known can be used, and examples thereof include the *Escherichia coli* BL21 (DE3) strain, K12 strain, DH1 strain, and JM109 strain. As *Escherichia coli* strains, in particular, the K12 strains and strains prepared therefrom-that is, so-called K strains-can be used. An example of the *Bacillus subtilis* strain is the *Bacillus subtilis* 168 strain.

Any promoter can be used, provided that it allows a gene of interest to be expressed in a host such as *Escherichia coli*. Examples thereof include *Escherichia coli*-derived promoters, such as trp promoters, lac promoters, PL promoters, and PR promoters, and phage-derived promoters, such as T7 promoters. Artificially designed and/or modified promoters, such as tac promoters, may also be used.

An expression vector can be introduced by any method, provided that such method is intended to introduce DNA into bacteria. Examples thereof include a method involving the use of calcium ions (Cohen, S. N. et al., Proc. Natl. Acad. Sci., U.S.A., 69: 2110-2114, 1972) and electroporation.

Examples of yeast strains that can be used for host microorganisms include, but are not particularly limited to, *Candida* yeast strains, such as *Candida Shehatae*, *Pichia* yeast strains, such as *Pichia stipites*, *Pachysolen* yeast strains, such as *Pachysolen tannophilus*, *Saccharomyces* yeast strains, such as *Saccharomyces cerevisiae*, and *Schizosaccharomyces* yeast strains, such as *Schizosaccharomyces pombe*, with *Saccharomyces cerevisiae* being particularly preferable.

When the expression level of the acyl-CoA reductase is to be enhanced, an adequate promoter with high transcriptional activity is used. Examples of promoters that can be used include, but are not particularly limited to, glyceraldehyde-3-phosphate dehydrogenase gene (TDH3) promoters, 3-phosphoglycerate kinase gene (PGK1) promoters, and hyperosmolarity-responsive 7 gene (HOR7) promoters. Pyruvate decarboxylase gene (PDC1) promoters are particularly preferable because of their high capacity for enhancing the expression level of the target downstream genes. Also, gal1 promoters, gal10 promoters, heat shock protein promoters, MFα1 promoters, PHO5 promoters, GAP promoters, ADH promoters, or AOX1 promoters may be used, so that the expression level of the downstream genes can be enhanced.

As methods for introducing the genes described above, any conventional techniques that are known as yeast transformation techniques can be employed. Specific examples include, but are not limited to, the electroporation method (Meth. Enzym., 194, p. 182, 1990), the spheroplast method (Proc. Natl. Acad. Sci., U.S.A., 75, p. 1929, 1978), the lithium acetate method (J. Bacteriology, 153, p. 163, 1983), and methods described in Proc. Natl. Acad. Sci., U.S.A., 75, p. 1929, 1978 and Methods in Yeast Genetics, 2000 Edition: A Cold Spring Harbor Laboratory Course Manual.

The nucleic acid encoding the acyl-CoA reductase is preferably introduced into a microorganism capable of hydrocarbon synthesis with the use of an aldehyde compound as a substrate. In such a case, a recombinant microorganism expressing the acyl-CoA reductase can produce a hydrocarbon from an aldehyde compound with high efficiency. For example, a nucleic acid encoding an enzyme having decarbonylase activity (i.e., a decarbonylase) may be introduced into the microorganism, and a recombinant microorganism capable of hydrocarbon synthesis from an aldehyde compound can then be produced. The recombinant microorganism thus obtained or a microorganism that inherently has decarbonylase activity may be used as a host, the acyl-CoA reductase may be introduced into such host, and hydrocarbon synthesis can then be carried out with very high efficiency.

Enzymes having decarbonylase activity are not particularly limited, and conventional enzymes can be used. For example, WO 2006/109558 discloses a method in which novel microalgae, *Pseudochoricystis ellipsoidea*, capable of hydrocarbon production or microalgae of *Pseudochoricystis* or *Choricystis* capable of hydrocarbon production are cultured and a hydrocarbon is collected from the culture product. A nucleic acid encoding an enzyme having decarbonylase activity can be isolated from such an organism and used. Also, the gene converting an aldehyde into an alkane disclosed in JP 2010-528627 A and the alkane synthase gene or the aldehyde synthase gene derived from *Synechococcus elongatus* disclosed in JP 2011-520455 A can be used. In addition, a gene encoding a protein involved with aliphatic aldehyde decarbonylase activity derived from *Arabidopsis thaliana* disclosed in JP H09-322780 A (1997) can be used.

Further, WO 2013/129393 discloses a hydrocarbon synthase gene encoding an enzyme comprising a given motif sequence and having decarbonylase activity. With the use of the hydrocarbon synthase gene disclosed in WO 2013/129393, hydrocarbons as described above can be produced with high efficiency.

A recombinant microorganism that comprises an introduced nucleic acid encoding decarbonylase (e.g., recombinant *Escherichia coli* or recombinant yeast) would be capable of synthesizing a hydrocarbon from an aldehyde compound in the presence of an aldehyde compound and a coenzyme, such as NADH, through the expression of the decarbonylase.

Examples of hydrocarbons that can be synthesized include a hydrocarbon having a chain structure (i.e., a chain hydrocarbon) and a hydrocarbon having a cyclic structure (i.e., a cyclic hydrocarbon). A chain hydrocarbon may have one or more branches. Examples of branches include alkyl groups, such as methyl, ethyl, propyl, and butyl (including tert-butyl) groups, alkynyl groups, and alkenyl groups. Further examples of branches include chloromethyl, acetyl, 2-pyridyl, hydroxyphenyl, aminoacetyl, methoxy, phenoxy, methylthio, and phenylthio groups. Also, hydrocarbons to be synthesized may be saturated hydrocarbons (alkane) or unsaturated hydrocarbons (alkene and alkyne).

It is preferable that a hydrocarbon to be synthesized have about 5 to 20 carbon atoms, which is liquid at room temperature, although the number of carbon atoms is not limited thereto. A hydrocarbon to be synthesized is preferably a saturated hydrocarbon having 10 to 20 carbon atoms, more preferably 12 to 14 carbon atoms, and most preferably 13 carbon atoms, from the viewpoint of the application thereof for a diesel fuel. Specific examples of hydrocarbons to be synthesized include dodecane having 12 carbon atoms, tridecane having 13 carbon atoms, and tetradecane having 14 carbon atoms.

[Method for Substance Production]

As described above, the recombinant microorganism according to the present invention has excellent activity for synthesizing an aldehyde compound using acyl-CoA as a substrate. With the use of the recombinant microorganism according to the present invention, therefore, at least one compound selected from the group consisting of an aldehyde compound and an alcohol and a hydrocarbon synthesized from an aldehyde compound can be produced.

For example, the recombinant microorganism according to the present invention is cultured in a medium containing a carbon source, such as glucose, fructose, galactose, mannose, xylose, xylulose, ribose, erythrose, threose, erythrulose, glyceraldehyde, dihydroxyacetone, sucrose (saccharose), lactose, maltose, trehalose, or cellobiose. Thus, a target substance, such as the aldehyde compound, alcohol, or hydrocarbon as described above, can be produced.

The recombinant microorganism according to the present invention can also be used for a method for producing a target substance in vitro. For example, the recombinant microorganism according to the present invention is ground, the resulting solution containing the ground microorganism is used, and a target substance can then be synthesized in vitro. Specifically, acyl-CoA (a coenzyme such as NADH, if necessary) is added as a substrate to the solution, and a target substance can then be synthesized in vitro.

A target substance, such as a synthesized hydrocarbon, can be isolated in accordance with a conventional technique. For example, the recombinant yeast is cultured in a medium to produce a hydrocarbon. Since a hydrocarbon is synthesized in a medium, strains are separated from the medium via centrifugation or other means, and the target substance can then be isolated from the supernatant fraction. A hydrocarbon can be isolated from the supernatant fraction by, for example, adding an organic solvent, such as ethyl acetate or methanol, to the supernatant fraction and thoroughly agitating the solution. The aqueous phase is separated from the solvent phase, and a hydrocarbon can be extracted from the solvent phase.

EXAMPLES

Hereafter, the present invention is described in greater detail with reference to examples, although the technical scope of the present invention is not limited to these examples.

Example 1

In this example, an expression vector comprising the aldehyde decarbonylase gene (Gene ID: Npun R1711) derived from *Nostoc punctiform* and an expression vector comprising a gene encoding a protein comprising the amino acid sequence of SEQ ID NO: 2, which had been isolated from *K. pneumoniae* subsp. *pneumoniae* NBRC3321 (this gene is hereafter referred to as the "acyl-CoA reductase gene"), were introduced into *Escherichia coli* strains, and the alkane productivity of the resulting recombinant *Escherichia coli* strains was evaluated.

In this example, the full-length sequence of the acyl-CoA reductase gene was determined in the manner described below and the acyl-CoA reductase gene was artificially synthesized based on the determined full-length sequence. At the outset, the *K. pneumoniae* subsp. *pneumoniae* NBRC3321 cell extract was fractionated using columns on the basis of aldehyde synthesizing activity as an index, and the acyl-CoA reductase protein was purified. Subsequently, the N-terminal amino acid sequence of the purified protein was determined. Primers were then designed based on the determined N-terminal amino acid sequence, and the full-length sequence of the acyl-CoA reductase gene was determined by PCR using the primers.

More specifically, cells were ultrasonically ground and centrifuged at 20,000×g for 30 minutes. The resulting supernatant was designated to be a cell-free extract. The resulting cell-free extract was subjected to ultracentrifugation at 100,000×g for 60 minutes, and a soluble fraction was obtained as the supernatant. The resulting soluble fraction was subjected to gel filtration column chromatography using Hiload 20/60 Superdex 200 pg, and fractions having activity of an acyl-CoA reductase were collected. Thereafter, the collected fractions were subjected to anion exchange column chromatography using MonoQ 10/100 GL, and fractions having activity of an acyl-CoA reductase were collected. Further, the collected fractions were subjected to gel filtration column chromatography using Superdex 200 10/300, and fractions having activity of an acyl-CoA reductase were collected. When assaying acyl-CoA reductase activity, at the outset, 1 µmol of tetradecanoyl-CoA, 5 µmol of NADH, 5 µmol of NADPH, 10 µmol of 2-mercaptoethanol, 20 µmol of potassium phosphate buffer (pH 8.0), and a crude enzyme solution were mixed, and the mixture was subjected to incubation at 37° C. for 16 hours. Thereafter, tetradecanal contained in the reaction solution was measured using a gas chromatography mass spectrometer (GC/MS) so as to evaluate the acyl-CoA reductase activity of the crude enzyme solution. Protein componenta contained in the crude enzyme solution were developed using SDS-PAGE and then electroblotted on the Sequi-Blot PVDF membrane. Thereafter, the N-terminal amino acid sequence of the enzyme was determined by the automated Edman degradation method using the PPSQ-33A protein sequencer.

Genomic DNA of the *K. pneumoniae* subsp. *pneumoniae* NBRC3321 was prepared in the manner described below. Specifically, the cultured cells were collected via centrifugation at 6,500×g for 10 minutes, and genome DNA was extracted using the DNeassy Blood & Tissue Kit (QIAGEN).

The acyl-CoA reductase gene was amplified by PCR using the obtained genome DNA as a template and the resultant was cloned into the pET-21b (+) vector. PCR was carried out using the sets of primers shown in Table 2. The underlined region in the table is the NdeI recognition sequence.

TABLE 2

| Primer | Nucleotide sequence | SEQ ID NO: |
|---|---|---|
| acrI F | 5'-CGCGC<u>CATATG</u>AATCAACAGGAC-3' | SEQ ID NO 12 |
| acrI R | 5'-TACGATTCGAAACGCATCCACCAG-3' | SEQ ID NO 13 |

A PCR solution was composed of 10 ng of genome DNA, 0.2 mM each dNTP, 0.25 mM each primer, and 0.02 units/µl of KOD FX neo DNA polymerase (Toyobo). PCR was carried out at 94° C. for 2 minutes, followed by 30 cycles each consisting of 98° C. for 10 seconds, 68° C. for 1 minute, and 72° C. for 10 minutes. Thereafter, the amplified fragment was processed with NdeI and HindIII, and the resultant was ligated to the pET-21b(+) vector, which had been processed with the same restriction enzymes. The full-length nucleotide sequence of the acyl-CoA reductase gene was determined using the resulting vector.

The aldehyde decarbonylase gene used in this example was artificially synthesized on the basis of the nucleotide sequence information stored in the database. SEQ ID NOs: 14 and 15 show the nucleotide sequence and the amino acid sequence of the aldehyde decarbonylase gene (Gene ID: Npun R1711), respectively.

The acyl-CoA reductase gene isolated in the manner described above was inserted into the NdeI-XhoI site of the pCDFDuet-1 vector (Novagen), and the artificially synthesized aldehyde decarbonylase gene was inserted into the Pst1 site of the pRSFDuet-1 vector (Novagen) (see FIG. 1). When isolating the acyl-CoA reductase gene, the sequence: TACCATGGGCATACATATGGCCATCATAACGGT-TCTGGCAAATATTCTGAAATGA GCTGTTGACAAT-TAATCATCGGCTCGTATAATGTGTGGAATTGT-GAGCGGATAAC AATTTCACACAAGGAGATATACG (SEQ ID NO: 16) comprising the NdeI recognition sequence was added to the 5' terminus, and the sequence: TAAT-TAACCTAGGCTGCTGCCACCGCTGAG-CAATAACTAGCATAACCCCTTGGGG CCTCTAAACGGGTCTTGAGGGGTTTTTTGCCCTC-GAGTCCGGCCGCATGCGGCCG CAT (SEQ ID NO: 17) comprising the XhoI recognition sequence was added to the 3' terminus.

Subsequently, the two types of prepared expression vectors were transformed into the *E. coli* BL21 (DE3) strain. Transformation was carried out by preparing *E. coli* BL21 (DE3) competent cells with reference to User Protocol TB009 Rev. F0104 (Novagen).

Subsequently, the resulting transformant was subjected to shake culture in 0.5 ml of LB medium, which contains 30 mg/ml streptomycin and 50 mg/ml kanamycin, at 37° C. and 130 rpm overnight. The culture solution was inoculated into 2 ml of M9 medium, which contains 2% glucose, 0.1% yeast extract, 30 mg/ml streptomycin, and 50 mg/ml kanamycin, to an amount of 1% therein by volume, and shake culture was conducted at 37° C. and 130 rpm for about 4 hours (final absorption: OD 600 of 0.4 to 0.6). Isopropyl β-D-1-thiogalactopyranoside (IPTG) was added to the culture solution to a final concentration of 1 mM therein, and culture was conducted at 37° C. and 130 rpm for 3 days.

The culture solution (1 ml) was sampled in a 1.5-ml Eppendorf tube, the bacterial strains were collected using a centrifuge (6,000 rpm, 1 minute, room temperature), and the supernatant was removed. Ethyl acetate (100 ml) was added to the pellets, and a suspension was prepared via vortex for about 1 minute. The resultant was centrifuged at 10,000 rpm for 1 minute at room temperature, and the resulting supernatant was then subjected to GC/MS analysis. The conditions for GC/MS analysis are shown in Table 3.

TABLE 3

| [GC/MS analysis conditions] |
|---|
| Column: HP-5MS (Agilent: 19091S-433) |
| Inlet temperature: 260° C. |
| Detector temperature: 260° C. |
| Split ratio: 1/20 |
| Carrier gas: He 1.0 ml/min |
| Oven heating conditions |
| 60° C., 1 min |
| Raised to 260° C. at 50° C./min |
| 260° C., 1 min |

Figure 2:
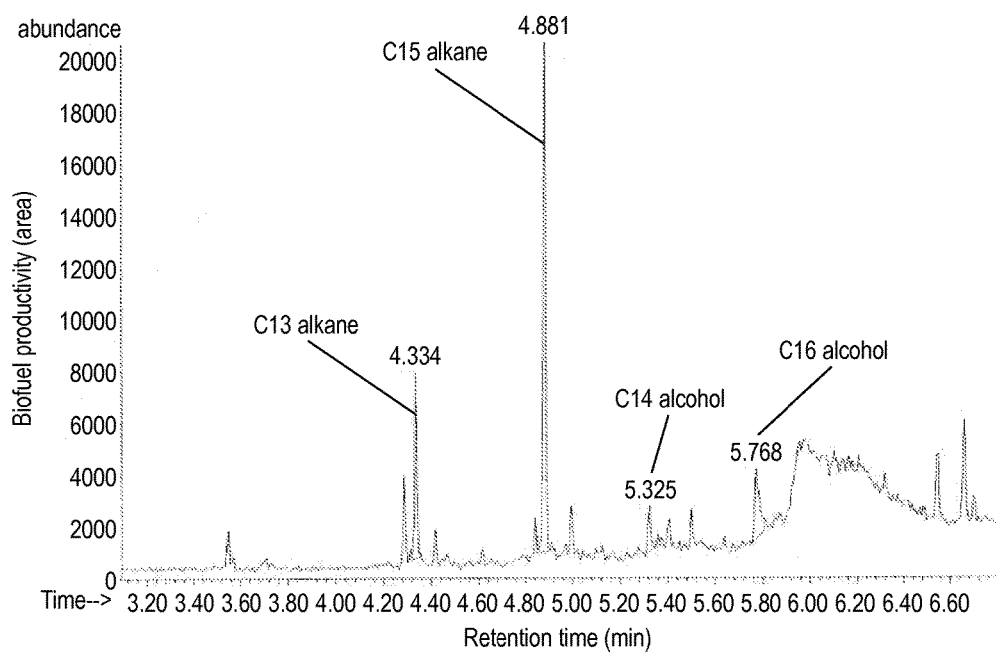
FIG. 2 shows a characteristic diagram demonstrating the results of GC/MS analysis of the suspension comprising ground recombinant E. coli cells prepared in examples.

FIG. 2 shows a chart demonstrating the results of GC/MS analysis regarding the recombinant *Escherichia coli* strains prepared in this example. As shown in FIG. 2, the recombinant *Escherichia coli* strains prepared in this example were found to be able to produce an alcohol having 14 carbon atoms, an alcohol having 16 carbon atoms, an alkane having 13 carbon atoms, and an alkane having 15 carbon atoms. The results demonstrate that the recombinant *Escherichia coli* strains prepared in this example had achieved the capacity to produce an aldehyde compound from acyl-CoA upon introduction of the acyl-CoA reductase gene. In other words, the acyl-CoA reductase gene that had been introduced into the recombinant *Escherichia coli* strains prepared in this example was found to encode acyl-CoA reductases having activity for reducing acyl-CoA to generate an aldehyde compound in the host microorganisms.

All publications, patents, and patent applications cited herein are incorporated herein by reference in their entirety.

The invention claimed is:

1. A recombinant microorganism comprising a nucleic acid encoding a protein (a) or (b) below introduced into a host microorganism, wherein the nucleic acid encoding the protein (a) or (b) is exogenous:
  (a) a protein comprising the amino acid sequence of SEQ ID NO: 2; or
  (b) a protein comprising an amino acid sequence having 95% or higher identity to the amino acid sequence of SEQ ID NO: 2 and having activity for synthesizing an aldehyde compound from acyl-CoA,
  and wherein said recombinant microorganism has aldehyde decarbonylase activity for synthesizing a hydrocarbon using an aldehyde as a substrate.

2. The recombinant microorganism according to claim 1, wherein the host microorganism is selected from the group consisting of *Escherichia coli*, *Corynebacterium*, and yeast.

3. The recombinant microorganism according to claim 1, wherein the host microorganism comprises a nucleic acid encoding an aldehyde decarbonylase that synthesizes a hydrocarbon using an aldehyde as a substrate.

4. The recombinant microorganism according to claim 1, which produces a hydrocarbon comprising a carbon chain of 13 to 15 carbon atoms.

5. A method for producing a substance comprising a step of culturing the recombinant microorganism according to claim 1 in a medium containing a carbon source and a step of recovering a target substance from the cultured recombinant microorganism.

6. The method for producing a substance according to claim 5, wherein the target substance is at least one member selected from the group consisting of an aliphatic aldehyde, an aliphatic alcohol, and a hydrocarbon.

7. A method for producing a substance comprising a step of culturing the recombinant microorganism according to claim 2, in a medium containing a carbon source and a step of recovering a target substance from the cultured recombinant microorganism.

8. A method for producing a substance comprising a step of culturing the recombinant microorganism according to claim 3, in a medium containing a carbon source and a step of recovering a target substance from the cultured recombinant microorganism.

9. A method for producing a substance comprising a step of culturing the recombinant microorganism according to claim 4, in a medium containing a carbon source and a step of recovering a target substance from the cultured recombinant microorganism.

* * * * *